(12) United States Patent
Foster et al.

(10) Patent No.: US 7,252,720 B2
(45) Date of Patent: Aug. 7, 2007

(54) REMOVAL OF PRION INFECTIVITY

(75) Inventors: Peter Reynolds Foster, Edinburgh (GB); Brenda Doreen Griffin, Edinburgh (GB); Ronald Vance McIntosh, North Berwick (GB)

(73) Assignee: Common Services Agency, Edinburgh (GB)

( * ) Notice: Subject to any disclaimer, the term of this patent is extended or adjusted under 35 U.S.C. 154(b) by 0 days.

(21) Appl. No.: 10/518,471

(22) PCT Filed: May 30, 2003

(86) PCT No.: PCT/GB03/02378

§ 371 (c)(1),
(2), (4) Date: Aug. 15, 2005

(87) PCT Pub. No.: WO03/105911

PCT Pub. Date: Dec. 24, 2003

(65) Prior Publication Data

US 2006/0096619 A1    May 11, 2006

(30) Foreign Application Priority Data

Jun. 18, 2002    (GB) ................... 0214007.7

(51) Int. Cl.
*B08B 3/04* (2006.01)
(52) U.S. Cl. ............... 134/42; 422/37; 422/28; 134/2; 134/22.1; 134/22.11; 134/22.13; 134/22.16; 134/22.17; 134/26; 134/29; 134/34; 134/36

(58) Field of Classification Search ............ 422/37, 422/28; 134/42, 2, 22.1, 22.11, 22.13, 22.16, 134/22.17, 26, 29, 34, 36
See application file for complete search history.

(56) References Cited

U.S. PATENT DOCUMENTS

| 5,808,011 | A | 9/1998 | Gawryl et al. |
| 6,221,614 | B1 * | 4/2001 | Prusiner et al. ............... 435/7.1 |
| 6,720,355 | B2 * | 4/2004 | Prusiner et al. ............. 514/557 |
| 6,831,161 | B1 * | 12/2004 | Uhlen et al. ................. 530/413 |
| 2002/0041859 | A1 * | 4/2002 | Prusiner et al. .......... 424/70.24 |
| 2003/0086820 | A1 * | 5/2003 | McDonnell et al. .......... 422/28 |
| 2003/0148385 | A1 * | 8/2003 | Antloga et al. .............. 435/7.1 |
| 2003/0162225 | A1 * | 8/2003 | James et al. ................. 435/7.1 |
| 2003/0175362 | A1 * | 9/2003 | Kross et al. ................ 424/718 |

(Continued)

FOREIGN PATENT DOCUMENTS

JP    2001-582013    *    8/2003

(Continued)

OTHER PUBLICATIONS

Turk, E. et al. "Purification and properties of the cellular and scrapie hamster prion proteins" *Bur. J. Biochem.* 176: 21-30 (1988).

(Continued)

*Primary Examiner*—Sharidan Carrillo
(74) *Attorney, Agent, or Firm*—Myers Bigel Sibley & Sajovec, P.A.

(57) ABSTRACT

Prion infectivity adsorbed onto substrates (for example, chromatographic columns used to fractionate blood plasma) is removed by treatment with 2M sodium chloride. Optionally, the substrate is further washed with 0.1 M sodium hydroxide.

10 Claims, 1 Drawing Sheet

U.S. PATENT DOCUMENTS

| | | | | |
|---|---|---|---|---|
| 2003/0198571 A1* | 10/2003 | Lynch | .................... | 422/28 |
| 2004/0171071 A1* | 9/2004 | Stefas | .................... | 435/7.1 |
| 2005/0050040 A1* | 3/2005 | Theobald et al. | .............. | 707/4 |
| 2006/0096619 A1* | 5/2006 | Foster et al. | ................. | 134/42 |

FOREIGN PATENT DOCUMENTS

| | | |
|---|---|---|
| WO | 2000-043782 A | 7/2000 |
| WO | 2001-054736 A | 8/2001 |

OTHER PUBLICATIONS

James, T.L. et al. "Solution structure of the 142-residue recombinant prion protein corresponding to the infectious fragment of the scrapie isoform" *PNAS* 94,:10086-10097 (1997).

Safar, J et al. "Eight prion strains have PrP$^{Sc}$ molecules with different conformations" *Nature Medicine* 4(10): 1157-1165 (1998).

Polymenidou, M. "A short purification process for quantitative isolation of PrP$^{Sc}$ from naturally occurring and experimental transmissible spongiform encephalopathies" *BMC Infectious Diseases* 2(23) (2002).

Silveria, J.R. et al. "The most infectious prion protein particles" *Nature* 437: 257-261 (2005) (including supplementary information pp. 1-14).

Meyer, R.K. "A monomer-dimer equilibrium of a cellular prion protein (PrP$^C$) not observed with recombinant PrP*" *J. Biol. Chem.* 275(48): 28081-38087 (2000).

Castilla, J. et al. "In vitro generation of infectious scrapie protein" *Cell* 121: 195-206 (2005).

EEC Regulatory Document, Notes for Guidance: Guidelines for Minimizing the Risk of Transmitting Agents Causing Spongiform Encephalopathy via Medicinal Products, *Biologicals* 20: 155-158 (1992).

Riesner, D. "Biochemistry and Structure of $PrP^{C}$ and $PrP^{Sc}$" *British Medical Bulletin* 66: 21-33 (2003).
Bennion, B. "Protein conformation and diagnostic tests: the prion protein" *Clinical Chemistry* 48(12): 2105-2114 (2002).
Brimacombe et al. "Characterization and polyanion-binding properties of purified recombinant prion protein", *Biochemical Journal* 342:605-613 (1999).
Dormont, D. "Agents that cause transmissible subacute spongiform encephalopathies", *Biomedicine & Pharmacotherapy* (1999).
Pan et al. "Purification and properties of the cellular prion protein from Syrian hamster brain", *Protein Science* 1:1343-1352 (1992).
Notification of Transmittal of the International Search Report or the Declaration, corresponding to PCT/GB03/02378, mailed Sep. 18, 2003.

* cited by examiner

REMOVAL OF PRION INFECTIVITY

RELATED APPLICATIONS

This application claims priority under 35 U.S.C. § 371 from PCT Application No. PCT/GB03/02378, filed in English on May 30, 2003, which claims the benefit of Great Britain Application Serial No. 0214007.7 filed on Jun. 18, 2002, the disclosures and contents of which are incorporated by reference herein in their entireties.

BACKGROUND OF THE INVENTION

The present invention relates to the cleaning of substrates, generally reusable substrates, in order to remove adsorbed prion infectivity. It particularly involves the cleaning of reusable chromatography columns employed during the processes involved in the fractionation of blood plasma. However, it also applies to the cleaning of other substrates, such as surgical instruments etc.

Prion-related disease is believed to be due to prion proteins having altered three-dimensional structure. However, the identification of the infective prion agent has not yet been conclusively resolved. In the present specification we refer to "prion infectivity" as covering the infective agent causative of prion-related disease (whatever that may be). The experimental methods described herein in fact measure prion infectivity in mice.

It is well known that prion infectivity adheres strongly to substrates by a unknown mechanism and means for reliably cleaning such substrates have hitherto been unknown as they will not normally withstand the severe conditions recommended for the inactivation of prion agents such as treatment with 2 M sodium hydroxide combined with heating at 121-138° C. (Taylor D M. Inactivation of prions by physical and chemical means. *J Hospital Infection* 1999; 43 Suppl.: S69-76).

Bovine spongiform encephalopathy (BSE) is a fatal neurodegenerative disorder of cattle, first described in the UK in 1987. Cases of BSE have since been discovered in over twenty different countries with almost 184 000 cases reported world-wide, 99% of which have occurred in the UK. The emergence of a new neurodegenerative disorder in humans, named variant Creutzfeldt-Jakob disease (vCJD), was subsequently shown to have been due to the BSE agent having been transmitted to humans, probably via the ingestion of diseased animal tissue. By June 2002, the numbers of confirmed or probable cases of vCJD reported were 122 in the UK, 6 in France and 1 in Italy. Individual cases of vCJD have also been reported in Ireland, Hong Kong and in the USA in persons who were resident in the UK previously. However, in the absence of a suitable diagnostic screening test, the prevalence of asymptomatic vCJD in the UK population or elsewhere is not known.

Although other forms of Creutzeldf-Jakob disease (CJD) have been transmitted iatrogenically by a number of medical procedures there is no evidence of such transmission by blood, blood products or plasma derivatives. Nevertheless, lack of knowledge over the prevalence of asymptomatic vCJD, together with the detection of abnormal prion protein in lympho-reticular tissues of individuals infected with vCJD had led to concern that vCJD may be transmitted by blood products. A risk analysis commissioned by the UK Department of Health concluded that there was a theoretical risk of vCJD being transmitted by plasma derivatives prepared from infected donations.

Considerable work has been done on the study of prions and general background information is provided in Stanley B. Prusiner et al "Some Strategies and Methods for the Study of Prions" Chapter 15, Prion Biology and Diseases, 1999 Cold Spring Harbor Laboratory Press. An assessment of the potential of blood plasma fractionation processes to remove the causative agents of transmissible spongiform encephalopathy (TSE) such as CJD or vCJD is given in P. R Foster, Transfusion Medicine, 1999, 9, 3-14 and a review of prions and blood products is given in P R Foster, Annals of Medicine 2000; 32: 501-513. Work presented in P. R. Foster et al, Vox Sang 2000; 78, 86-95, identified depth filtration, particularly using a Seitz KS80 depth filter as being particularly effective in removing prion proteins from blood plasma fractionations streams. Other attempts to remove prion proteins are described in patent application PCT/FR97/00465 which employs a combination of electrostatic adsorption and chromatography; and patent U.S. Pat. No. 5,808,011 which removes prion infectivity from a solution by adsorption of the prion to a chromatography column by use of a pH gradient.

Thus, whilst there is a growing understanding of ways in which prions can be removed from process streams, particularly those involved in blood fractionation, the fate of prion infectivity remains uncertain. Thus, there is a serious risk that prion agents immobilised on chromatography columns during the processing of one batch of blood plasma, may remain during the processing of subsequent batches leading to possible contamination thereof It is therefore important to be able to know with certainty that reusable chromatography columns (which may have a reusable lifetime of several years) can be reliably cleaned of prion infectivity at the end of each batch run. Furthermore, there is a concern that other medical or surgical substrates, such as surgical instruments may also be effective in transmitting CJD. Flechsig E. et al, Mol. Med 2001 October; 7(10): 679-684 reports that prions are readily and tightly bound to stainless steel surfaces and that electrodes used intracerebrally on CJD patients transmitted the disease to two further patients and finally to a chimpanzee, despite attempted disinfection. The UK Department of Health has also assessed the risk of prion infectivity being transmitted to patients via instruments used in surgery and other invasive medical procedures, concluding that "variant and sporadic CJD may be transmitted on surgical instruments" and "current procedures for decontaminating surgical instruments between uses cannot be guaranteed to eliminate the abnormal prion proteins that are thought to be responsible for the transmission of CJD." (CJD Incidents Panel. Management of possible exposure to CJD through medical procedures: a consultation paper. *Department of Health Publications*, October 2001). Similarly, there is concern that prion diseases may be transmitted during eye surgery as opthalmic instuments can remain contaminated with debris after cleaning (Dinakaran S, Kayarkar V V. *Eye* 2002; 16: 281-284). There is therefore a need to reliably clean substrates involved in medical or surgical procedures on patients, so as to avoid the transmission of prion-related disease.

SUMMARY OF THE INVENTION

We have now surprisingly found that the use of concentrated solutions of salts, such as sodium chloride, are effective in eluting or completely removing adsorbed prion infectivity.

Thus, one aspect of the present invention provides a method of cleaning a substrate (particularly a reusable substrate) in order to remove adsorbed prion infectivity which comprises washing the substrate with a concentrated salt solution of a concentration of at least 1.0M.

Another aspect of the invention provides a salt solution of a concentration of at least 1.0M for use in cleaning a substrate in order to remove adsorbed prion infectivity.

DETAILED DESCRIPTION OF THE INVENTION

Figure 1:
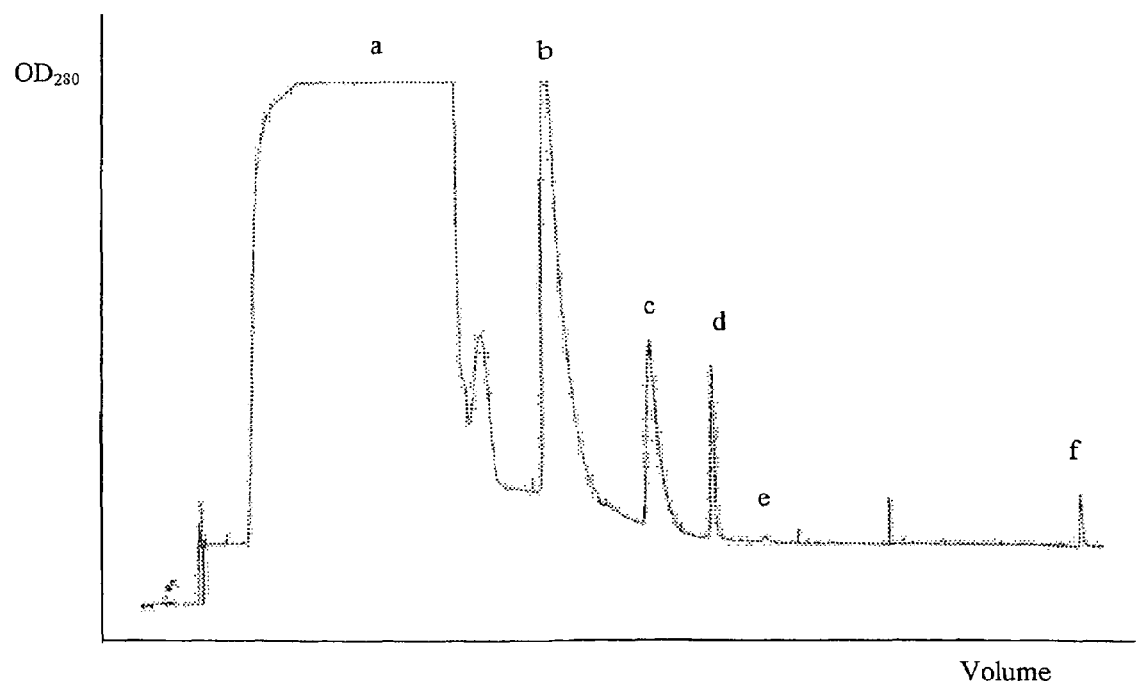
FIG. 1 shows the optical density of a solution being eluted from ion exchange chromatography of intermediate purity Factor VIII solution spiked with BSE-301 V microsomal fraction. a=Fibrogen fraction (110 mM NaCl); b=von Willebrand Factor fraction (145 mM NaCl); c=Factor VIII fraction (250 mM NaCl); d=First sodium chloride wash (2M NaCl); e=sodium hydroxide wash (1.0M NaOH); f=Second sodium chloride wash (2M NaCl).

Thus, it has been found that washing the substrate, particularly a chromatographic column, with a salt solution of a concentration of least 1.0M, particularly 1.5M, especially 1.75M and preferably at least 2.0M is effective in removing adsorbed prion infectivity. It was a surprising result to us that the prion infectivity appeared to follow conventional ion exchange behaviour with an anion exchange matrix and could be eluted by high salt concentrations. In fact, this is so unexpected that our initial experimental protocol was not optimised for measuring prion infectivity levels eluted with the salt washes.

In principle, any salt which is pharmaceutically, medically or surgically acceptable in the context of the particular process involved may be used. Usually, inexpensive salts are employed. Sodium chloride is a preferred salt but sodium citrate, sodium acetate, sodium gluconate, sodium sulphate, potassium chloride, lithium chloride and ammonium chloride might also be employed. Thus, sodium, potassium and ammonium are preferred cations. Other salts may also be used where they provide a counter ion capable of displacing prion infectivity from solid phases.

The present invention may also be employed as a method for concentrating or purifying prion agents, involving adsorption onto a substrate, such as the chromatography column and eluting with concentrated salt solution. This invention may also be used for the recovery and preparation of prion agents for research purposes and in the processing of biological samples being tested for the presence of prion agents, effectively increasing the sensitivity of an overall procedures for the detection or quantitation of prions, such as in the testing of blood donations.

The present invention has wide applicability to the cleaning of substrates which may potentially have been contaminated with human or animal prion agents, by having been in contact with human or animal material, particularly bodily fluids. Thus, the invention may be applied to clean chromatographic materials but may also be used to clean pipes, vessels etc. employed in the processing of blood plasma or any other material where there is a risk of prion contamination. Substrates required in surgical procedures, such as surgical instruments, electrodes or other substrates brought into contact with the body may be cleaned by the method of the present invention. Meat processing equipment such as employed in abattoirs, including all types of tools and abattoir equipment may also be cleaned.

The cleaning method of the present invention may be applied to treat substrates involved in the fractionation of human plasma, such as described in P. R. Foster, Transfusion Medicine, 1999, 9, 3-14, particularly the production of plasma products including albumin, immunoglobulins, factor II, factor VII, factor IX, factor X, thrombin, factor VIII, fibrinogen, von Willebrand factor, anti-thrombin III, alpha-1-antitrypsin, factor III, C1-inhibitor, transferrin and mannose binding lectin. The chromatographic substrate involved in the fractionation is usually an adsorbent of the type used for purification of proteins or other macro molecules in a packed bed, chromatography column or other format (e.g. batch or fluidised adsorption). The invention may also be applied in the preparation of other bio-pharmaceutical preparations prepared from animal substances, including transgenic or other genetically modified material, or where human or animal-derived substances are used in the manufacturing process, such as in mammalian cell culture.

The process will generally be carried out at room temperature but may also be applied at any temperature compatible with the substrate and salt concerned e.g. in the temperature range 0° C. to 30° C.

The method may include one or more washing steps. In order to be assured of total prion removal, it is preferred to use a second and optionally subsequent washing step using the concentrated salt solution. The wash solution may be recovered and tested for prion infectivity.

The concentrated salt wash may be followed by a further washing step employed as alkali (such as sodium hydroxide, potassium hydroxide, lithium hydroxide; or the analogous carbonates or bicarbonates), generally of a concentration of 0.05 to 0.5M. Typically, this brings the pH to at least 12. Preferably, the substrate is allowed to soak at this pH for 0.5 to 2 hours. One or more alkali wash steps may be employed; preferably alternated with concentrated salt washes.

Where the procedure is used to clean a chromatographic column, the chromatographic substrate is generally an ion-exchange column of the type conventionally used in blood plasma fractionation but may also include chromatographic media used in affinity chromatography, size-exclusion chromatography, immuno-affinity chromatography and hydrophobic interaction chromatography (Burnouf T. Chromatography in plasma fractionation: benefits and future trends. *J Chromatography B* 1995; 664: 3-15). In addition the invention may be used to treat membrane systems in order to remove prion contamination prior to re-use of a membrane, such as in the purification or formulation of proteins by ultrafiltration or by dia-filtration.

Embodiments of the present invention will now be described by way of Example only in the following experimental work, which refers to the attached FIG. 1.

Desorption of Prions from Solid Phases.

EXAMPLE

Preparation of a Microsomal Fraction of BSE 301V as the 'Spiking' Inoculum

In order to study the partitioning behaviour of prions, an aliquot of infective material, in the form of a microsomal fraction derived from BSE-infected murine brain, was added to the starting Factor VIII solution. The procedure for the preparation of the microsomal inoculum was based on the method of Millson et al. (Millson G C, Hunter G D, Kimberlin R H. An experimental examination of the scarpie agent in cell membrane mixtures. II. The association of scrapie activity with membrane fractions. *J Comp Path* 1971; 81: 255-265).

Brain tissue (3 g), taken late in the clinical phase of disease from in-bred VM mice infected with murine-passaged BS8 (strain 301V), was suspended in 27 ml phosphate buffered saline (PBS), homogenised in a Dounce homogeniser and centrifuged at 2000 rpm for 10 minutes at 4° C. The pellet was resuspended in 10 ml PBS and centrifuged again under the same conditions. The supernatants recovered from both procedures were pooled and centrifuged at 10 000 g for 7 minutes in order to sediment unbroken cells, large fragments of cells, mitochondria and cell nuclei. The translucent supernatant was removed carefully and centrifuged at 100 000 g for 1 h at 4° C. in order to sediment the microsomal fraction. The supernatant was discarded and the pellet was resuspended in 30 ml PBS to provide the inoculum for 'spiking' the starting Factor VIII solution.

Ion Exchange Chromatography.

Microsomal inoculum (10 ml) was added to a solution of Factor VIII (102.7 ml) of intermediate purity, containing 20 mM trisodium citrate, 2.5 mM calcium chloride, 109 mM sodium chloride and 4.5% w/v sucrose. Polysorbate-80 and tri(n-butyl) phosphate were then added to the solution to obtain concentrations of 1% v/v and 0.3% v/v respectively and the resultant mixture (108.6 ml) stirred at 25±1° C. for 18 h prior to processing by ion exchange chromatography.

The ion exchange procedure was based on the method of Burnouf et al. (Burnouf T, Burnouf-Radosevich M, Huart J J, Goudemand M. A highly purified Factor VIII:c concentrate prepared from cryoprecipitate by ion-exchange chromatography. *Vox Sang* 1991; 60: 8-15). 14 ml DEAE-Toyopearl 650M (TosohBiosep GmbH, Stuttgart Germany) was packed into a 10 mm diameter column (C10/20, Pharmacia, Upsala, Sweden) using 2M sodium chloride and equilibrated with 130 ml of buffer containing 120 mM glycine, 16 mM lysine, 10 mM trisodium citrate, 1 mM calcium chloride and 110 mM sodium chloride at pH 7.0.

Solvent-detergent treated Factor VIII solution (98.6 ml) was applied to the column followed by 42 ml of equilibration buffer and the breakthrough (unadsorbed) fraction (139.8 ml) collected (Fibrinogen Fraction). 41 ml of equilibration buffer raised to 145 mM sodium chloride was then applied and the resultant fraction collected (von Willebrand Factor Fraction). This was followed by 26 ml of equilibration buffer raised to 250 mM sodium chloride which was used to elute Factor VIII (Factor VII Fraction).

Following collection of the Factor VIII eluate, the chromatography bed was treated with solutions of 2 M sodium chloride, 0.1 M sodium hydroxide and again with 2 M sodium chloride with the objective of removing proteins and other materials (eg. lipids) which remained bound to the ion exchange matrix. The extent to which prion infectivity might be removed by any of these procedures was not known. Therefore samples of these fractions were collected for analysis as well as the product eluates. First, 25 ml of 2 M sodium chloride was applied to the column and the eluate (15.5 ml) collected from the beginning of the 'salt front' (First NaCl Wash). Subsequently 0.1M sodium hydroxide (70 ml) was applied to the column and an eluate (39 ml) collected as the pH increased from 6.3 to >12 (NaOH wash). When the application of 0.1M sodium hydroxide was complete, the column was allowed to soak in sodium hydroxide for one hour and then subjected to a second wash with 2 M sodium chloride (42 ml). An eluate volume of 8.1 ml was collected to capture the protein eluted at this stage (Second NaCl wash).

Determination of Protein Being Eluted During the Ion-Exchange Process

Throughout the ion exchange procedure the output from the column was monitored continuously by in-line measurement of the solution optical density at a wavelength of 280 nm ($OD_{280}$) in order to detect protein (and other $OD_{280}$ absorbent material) being eluted. The $OD_{280}$ profile obtained is shown in FIG. 1.

Desorption of protein (or other material absorbent at $OD_{280}$) was thus observed during:

elution of the Fibrinogen Fraction (at 110 mM NaCL), elution of the von Willebrand Factor Fraction (at 145 mM NaCl), elution of the Factor VIII Fraction (at 250 mM NaCl), at the First Sodium Chloride Wash (at 2M NaCl), at the Sodium Hydroxide Wash (0.1 M NaOH), and at the Second Sodium Chloride Wash (at 2M NaCl).

Material eluted during the first 2 M sodium chloride wash was subsequently formed to have high prion infectivity.

Determination of BSE Infectivity

The BSE infectivity of samples from the ion exchange process was determined by a bioassay carried out at the Institute of Animal Health, West Mains Road, Edinburgh, UK. Samples for assay were diluted in saline and injected intracerebrally into weanling VM mice. Animals were observed carefully for up to 547 days and scored for clinical signs as described by Dickinson et al. (Dickinson A G, Meikle V M, Fraser I H. Identification of a gene which controls the incubation period of some strains of scrapie agent in mice. *J Comp Path* 1968; 78: 293-299). BSE infection in mice with clinical symptoms was confirmed by histopathological examination for brain vacuolation specific to prion diseases, as described by Bruce (Bruce M E. Strain typing studies of scrapie and BSE; in Baker H, Ridley R M, eds: *Methods in Molecular Medicine: Prion Diseases.* Totowa, N.J., Humana Press, 1996, pp 223-236).

Results

The numbers of mice infected with BSE at different sample dilutions are given in Table 1, together with the time taken for infection to be observed (mean incubation period). Both the original microsomal inoculum and the 'spiked' Factor VIII feedstock (prior to addition of solvent/detergent) exhibited a high degree of infectivity according to the proportion of mice infected and the relatively short mean incubation period (ie 131 days and 135 days respectively at $10^{-2}$ sample dilution). After addition of solvent/detergent the Factor VIII feedstock exhibited a similar degree of infectivity (result not shown). By contrast the Fibrinogen Fraction, the von Willebrand Factor Fraction and the Factor VIII Fraction all contained much less infectivity with the respective mean incubation periods of 204 days, 194 days and 166 days being inversely related to sodium chloride concentration, indicating that desorption of this small amount of prion infectivity followed conventional behaviour for the desorption of proteins from anion exchangers. All of the mice injected with the First NaCl Wash developed infection with a relatively short mean incubation period, demonstrating a very high degree of prion infectivity in this eluate. Thereafter no infectivity was detected in material desorbed from the column during either treatment with Sodium Hydroxide or the Second NaCl wash, despite further protein being eluted with 2 M NaCl following the treatment with sodium hydroxide. These data clearly demonstrate the effectiveness of the First NaCl wash in removing prion infectivity, most of which remained bound to the solid phase after the product fractions had been eluted.

In addition, the subsequent absence of BSE infectivity after treatment with 0.1M NaOH (either in the NaOH sample or in the second 2M NaCl wash) demonstrates that a combination of 2M NaCl followed by 0.1M NaOH was effective in removing all infectivity that could potentially have been desorbed in the second 2M NaCL wash.

TABLE 1

Incidence of BSE infection in mice inoculated with different samples from an anion exchange chromatography process used in the preparation of Fibrinogen and Factor VIII concentrate.

| SAMPLE | PARAMETER | SAMPLE DILUTION | | | | | | |
|---|---|---|---|---|---|---|---|---|
| | | $10^{-2}$ | $10^{-3}$ | $10^{-4}$ | $10^{-5}$ | $10^{-6}$ | $10^{-7}$ | $10^{-8}$ |
| BSE inoculum | mice infected/inoculated | 12/12 | | | | | | |
| | incubation period (days) | 131 ± 10 | | | | | | |
| Feedstock (spiked) | mice infected/inoculated | 6/6 | 6/6 | 5/6 | 4/6 | 0/12 | 0/10 | 0/11 |
| (prior to S/D addition) | incubation period (days) | 135 ± 11.4 | 145 ± 14.5 | 174 ± 12.5 | 198 ± 31.5 | — | — | — |
| Fibrinogen fraction | mice infected/inoculated | 7/12 | 0/11 | 0/11 | 0/12 | | | |
| (110 mM NaCl) | incubation period (days) | 204 ± 40.7 | — | — | — | | | |
| vWF fraction | mice infected/inoculated | 2/11 | | | | | | |
| (145 mM NaCl) | incubation period (days) | 194 ± 4.9 | | | | | | |
| Factor VIII fraction | mice infected/inoculated | 12/12 | 6/11 | 1/12 | 0/11 | 0/12 | | |
| (250 mM NaCl) | incubation period (days) | 166 ± 19.6 | 193 ± 8.6 | 245 | — | — | | |
| First NaCl wash | mice infected/inoculated | 6/6 | | | | | | |
| (2 M NaCl) | incubation period (days) | 138 ± 8.6 | | | | | | |
| NaOH wash | mice infected/inoculated | 0/5 | | | | | | |
| (0.1 M NaOH) | | | | | | | | |
| Second NaCl wash | mice infected/inoculated | 0/5 | | | | | | |
| (2 M NaCl) | | | | | | | | |

The invention claimed is:

1. A method of cleaning a substrate of chromatographic materials in order to remove adsorbed prion infectivity, comprising washing the substrate with a concentrated salt solution consisting of an aqueous solution of sodium chloride, having a concentration of at least 1.0 M.

2. The method according to claim 1, wherein the substrate is an adsorbent used in the purification of proteins or other macro molecules.

3. The method according to claim 1 wherein the salt solution has a concentration of at least 1.5 M.

4. The method according to claim 1, wherein the salt solution has a concentration of at least 1.75 M.

5. The method according to claim 1, wherein the method is employed to clean a substrate involved in the fractionation of human plasma.

6. The method according to claim 1, wherein washing the substrate with the concentrated salt solution is followed by washing with an alkali.

7. The method according to claim 1, comprising washing the substrate in a further step with the concentrated sodium chloride salt solution.

8. The method according to claim 6, wherein the alkali has a concentration of 0.05 M to 0.5 M.

9. The method according to claim 6, wherein the alkali brings the pH at the substrate to at least 12.

10. The method according to claim 6, wherein the substrate is contacted with the alkali for 0.5 to 2 hours.

* * * * *